United States Patent
Oliver

(10) Patent No.: US 7,404,944 B2
(45) Date of Patent: Jul. 29, 2008

(54) SULFATE REMOVAL FROM ETHANOL

(75) Inventor: Mitchell K. Oliver, Bartlesville, OK (US)

(73) Assignee: ConocoPhillips Company, Houston, TX (US)

( * ) Notice: Subject to any disclaimer, the term of this patent is extended or adjusted under 35 U.S.C. 154(b) by 195 days.

(21) Appl. No.: 11/408,707

(22) Filed: Apr. 21, 2006

(65) Prior Publication Data

US 2007/0249487 A1 Oct. 25, 2007

(51) Int. Cl.
*C01B 17/02* (2006.01)
*C07C 27/26* (2006.01)
*C07C 29/74* (2006.01)

(52) U.S. Cl. .................. 423/512.1; 568/913

(58) Field of Classification Search ............. 423/512.1; 568/913
See application file for complete search history.

(56) References Cited

U.S. PATENT DOCUMENTS

| 2,605,279 | A | | 7/1952 | Edwards et al. | |
| 2,700,690 | A | | 1/1955 | Mottern | |
| 3,071,445 | A | | 1/1963 | Gormley | 23/224 |
| 5,766,895 | A | | 6/1998 | Valkanas et al. | 435/161 |
| 2007/0131589 | A1 | * | 6/2007 | Weston et al. | 208/213 |
| 2007/0238907 | A1 | * | 10/2007 | Binder et al. | 568/913 |

OTHER PUBLICATIONS

PCT Application PCT/US96/18945, International Filing Date: Nov. 27, 1996, Ladisch et al., International Publication No. WO97/20079, Title: Modification of Corn Grits to Provide Superior Water Adsorption Characteristics.

* cited by examiner

*Primary Examiner*—Elizabeth D Wood
(74) *Attorney, Agent, or Firm*—Jeffrey R. Anderson

(57) ABSTRACT

A process for removing sulfates such as hydrogen sulfate, sodium sulfate, and chloride from an ethanol stream by contacting the ethanol stream with a clay material to thereby remove at least a portion of the sulfates.

16 Claims, No Drawings

SULFATE REMOVAL FROM ETHANOL

The present invention relates to a process for the removal of sulfate compound(s) from an ethanol stream. In another aspect, this invention relates to a process for the removal of sulfate compound(s) and/or chloride compound(s) from an ethanol stream. In another aspect, this invention relates to a process for the removal of hydrogen sulfate and/or sodium sulfate from ethanol.

Sulfates and chlorides are present in ethanol produced from corn. The sulfates can react with sodium in the ethanol distribution system to form sulfate salts. These salts become insoluble when gasoline is blended with ethanol and can plug service station filters. There is also some concern that these sulfate salts may deposit on fuel injectors in automobile engines. There currently exists no known method to remove sulfates from ethanol once it has been contaminated. Therefore, development of a process for effectively and efficiently removing sulfates and chlorides from ethanol would be a significant contribution to the art and to the economy.

BRIEF SUMMARY OF THE INVENTION

It is, thus, an object of the present invention to provide an effective process for removing sulfates from an ethanol stream.

It is yet another object of the present invention to provide an effective process for removing chlorides from an ethanol stream.

A further object of this invention is to provide an effective process for removing hydrogen sulfate and/or sodium sulfate from an ethanol stream.

In accordance with one aspect of the present invention, a process is provided including the following:

contacting a feed stream, comprising ethanol and a sulfate compound, with a clay material to thereby remove at least a portion of the sulfate compound from the feed stream to thereby produce a product stream comprising less of the sulfate compound than the feed stream.

In accordance with another aspect of the present invention, a process is provided including the following:

contacting a feed stream, comprising ethanol, a sulfate compound and a chloride compound, with a clay material to thereby remove at least a portion of the sulfate compound and the chloride compound from the feed stream to thereby produce a product stream comprising less of the sulfate compound and the chloride compound than the feed stream.

DETAILED DESCRIPTION OF THE INVENTION

According to the present invention, the feed stream comprises, consists of, or consists essentially of ethanol, water and a sulfate compound. The feed stream can alternatively comprise, consist of, or consist essentially of ethanol, water, a sulfate compound and a chloride compound. The feed stream can also alternatively comprise, consist of, or consist essentially of ethanol, a chloride compound, a sulfate compound, water, methanol, 1-propanol, 2-propanol, 1-butanol, 1-pentanol, 2-pentanol, 3-pentanol, natural gasoline, and gasoline. The sulfate compound concentration of the feed stream is typically greater than about 2 ppmw, more typically greater than about 3 ppmw, and most typically greater than about 4 ppmw. When present, the chloride compound concentration of the feed stream is typically greater than about 50 ppmw, more typically greater than about 60 ppmw, and mostly typically greater than about 80 ppmw.

The feed stream is contacted with a clay material to thereby remove at least a portion of the sulfate compound, and optionally the chloride compound, from the feed stream to thereby produce a product stream comprising less of the sulfate compound, and optionally less of the chloride compound, than the feed stream.

The concentration of the sulfate compound present in the product stream is preferably less than about 1.0 ppmw, more preferably less than about 0.6 ppmw, and most preferably less than about 0.4 ppmw. The concentration of the chloride compound present in the product stream is preferably less than about 40 ppmw, more preferably less than about 30 ppmw, and most preferably less than about 20 ppmw.

The sulfate compound can be any sulfate compound found to be present in an ethanol stream. Typically, the sulfate compound comprises a compound selected from the group consisting of hydrogen sulfate, sodium sulfate, and combinations thereof. Most typically, the sulfate compound is hydrogen sulfate.

The chloride compound can be any chloride compound found to be present in an ethanol stream.

The clay material can be any clay capable of removing sulfate compounds from ethanol. Preferably, the clay material is atapulgus.

The contacting of the feed stream with the clay material is preferably conducted at a temperature in the range of from about 0° F. to about 120° F.

The following examples are provided to further illustrate this invention and are not to be considered as unduly limiting the scope of this invention.

EXAMPLE

A one gallon sample of ethanol taken from a commercial ethanol production facility was contacted with atapulgus clay loaded in a canister-type filter. The sulfate concentration of the ethanol feed was 2.6 ppm. The effluent ethanol contained no detectable sulfates (less than 0.1 ppm). The sulfate concentrations were measured using Ion Chromatograpy (IC).

This example clearly demonstrates the effectiveness of clay in removing sulfates from ethanol.

While this invention has been described in detail for the purpose of illustration, it should not be construed as limited thereby but intended to cover all changes and modifications within the spirit and scope thereof.

That which is claimed:

1. A process comprising contacting a feed stream, comprising ethanol and a sulfate compound, with a clay material to thereby remove at least a portion of said sulfate compound from said feed stream to thereby produce a product stream comprising less of said sulfate compound than said feed stream.

2. A process in accordance with claim 1 wherein the concentration of said sulfate compound in said feed stream is greater than about 2 ppmw.

3. A process in accordance with claim 1 wherein the concentration of said sulfate compound in said feed stream is greater than about 3 ppmw.

4. A process in accordance with claim 1 wherein the concentration of said sulfate compound in said product stream is less than or equal to about 1.0 ppmw.

5. A process in accordance with claim 1 wherein the concentration of said sulfate compound in said product stream is less than or equal to about 0.6 ppmw.

6. A process in accordance with claim 1 wherein said sulfate compound comprises a compound selected from the group consisting of hydrogen sulfate, sodium sulfate, and combinations thereof.

7. A process in accordance with claim 1 wherein said clay material is atapulgus.

8. A process in accordance with claim 1 wherein said contacting is conducted at a temperature in the range of from about 0° F. to about 120° F.

9. A process comprising contacting a feed stream, comprising ethanol, a sulfate compound and a chloride compound, with a clay material to thereby remove at least a portion of said sulfate compound and said chloride compound from said feed stream to thereby produce a product stream comprising less of said sulfate compound and said chloride compound than said feed stream.

10. A process in accordance with claim 9 wherein the concentration of said sulfate compound in said feed stream is greater than about 2 ppmw, and wherein the concentration of said chloride compound in said feed stream is greater than about 50 ppmw.

11. A process in accordance with claim 9 wherein the concentration of said sulfate compound in said feed stream is greater than about 3 ppmw, and wherein the concentration of said chloride compound in said feed stream is greater than about 60 ppmw.

12. A process in accordance with claim 9 wherein the concentration of said sulfate compound in said product stream is less than or equal to about 1.0 ppmw, and wherein the concentration of said chloride compound in said product stream is less than or equal to about 40 ppmw.

13. A process in accordance with claim 9 wherein the concentration of said sulfate compound in said product stream is less than or equal to about 0.6 ppmw, and wherein the concentration of said chloride compound in said product stream is less than or equal to about 30 ppmw.

14. A process in accordance with claim 9 wherein said sulfate compound comprises a compound selected from the group consisting of hydrogen sulfate, sodium sulfate, and combinations thereof.

15. A process in accordance with claim 9 wherein said clay material is atapulgus.

16. A process in accordance with claim 9 wherein said contacting is conducted at a temperature in the range of from about 0° F. to about 120° F.

* * * * *